(12) United States Patent
Tomalia et al.

(10) Patent No.: US 7,078,461 B2
(45) Date of Patent: Jul. 18, 2006

(54) BIOCOMPATIBLE DENDRIMERS

(75) Inventors: Donald A. Tomalia, Midland, MI (US); Istvan J. Majoros, Ypsilanti, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 227 days.

(21) Appl. No.: 10/431,956

(22) Filed: May 8, 2003

(65) Prior Publication Data

US 2004/0151689 A1 Aug. 5, 2004

(Under 37 CFR 1.47)

Related U.S. Application Data

(63) Continuation of application No. 10/254,126, filed on Sep. 25, 2002, now abandoned, which is a continuation of application No. 10/039,393, filed on Oct. 26, 2001, now abandoned.

(51) Int. Cl.
*C08L 67/00* (2006.01)
*C08G 63/48* (2006.01)

(52) U.S. Cl. .................. 525/43; 525/50; 525/54.3; 525/55

(58) Field of Classification Search .................. 525/417, 525/374, 410
See application file for complete search history.

*Primary Examiner*—Jezia Riley
(74) *Attorney, Agent, or Firm*—Medlen & Carroll, LLP

(57) ABSTRACT

The present invention relates to compositions and methods involving biocompatible dendrimers. In particular, the present invention provides dendrimeric copolymers with poly(propyleneimine) (POPAM) interiors and poly (amidoamine) (PAMAM) exteriors for use in transfection and imaging applications.

14 Claims, 6 Drawing Sheets

E:\TABLECURVE3D\CLIPBRD.WK1
Rank 10 Eqn 1101 $z=(a+bx+cx^2+dx^3+ey)/(1+fx+gx^2+hy+iy^2)$
$r^2=0.99930329$ DF Adj $r^2=0.99804921$ FitStdErr=0.65648729 Fstat=1075.7368
a=36.164646 b=-20.572912 c=9.1528291 d=-1.1562782 e=7.9206639
f=-0.017209739 g=-0.0117181 h=0.030197484 i=-0.009491276

BIOCOMPATIBLE DENDRIMERS

The present Application is a Continuation of U.S. patent application Ser. No. 10/254,126, filed on Sep. 25, 2002 now abandoned, which is a Continuation of U.S. patent application Ser. No. 10/039,393 filed on Oct. 26, 2001, now abandoned.

This invention was made in part with Government support by the United States Army Research Laboratory Grant Number DAAL 01-96-2-0044, by the National Cancer Institute Grant Number NOI-CO-97111, by the National Institutes of Health Grant Number N01-AR-6-2226, and by the Defense Advanced Research Projects Agency Grant Number MDA972-97-1-0007. Accordingly, the Government has certain rights in the invention.

FIELD OF THE INVENTION

The present invention relates to compositions and methods involving biocompatible dendrimers. In particular, the present invention provides dendrimeric copolymers with poly(propyleneimine) (POPAM) interiors and poly (amidoamine) (PAMAM) exteriors for use in transfection and imaging applications.

BACKGROUND OF THE INVENTION

Dendrimers and hyperbranched polymers represent a novel class of structurally controlled macromolecules derived from a branches-upon-branches structural motif (Tomalia et al., *Angew. Chem. Intl. Edit.* 29:138–175 [1990]; and Naylor et al., *J. Am. Chem. Soc.* 111:2339–2341 [1989]). Dendrimers are well defined, highly-branched macromolecules that radiate from a simple organic molecule as a core and are synthesized through a stepwise, repetitive reaction sequence that guarantees complete shells for each generation leading theoretically to products that are unimolecular and monodisperse (Tomalia et al., *Macromolecule* 24:1435–1438 [1999]; and Dvornic and Tomalia, "Dendritic polymers divergent synthesis: starburst poly(amidoamine) dendrimers," in Salamone (ed.) *The Polymeric Materials Encyclopedia: Synthesis, Properties and Applications,*" (CRC Press: Boca Raton) [1996]). The synthetic procedures developed for dendrimer preparation permit nearly complete control over the critical molecular design parameters, such as size, shape and shell/core chemistry. Synthetic techniques that have proven effective for dendrimer production include the divergent strategy of Tomalia and co-workers (Tomalia et al., *Angew. Chem. Intl. Edit.* 29:138–175 [1990]; and Naylor et al., *J. Am. Chem. Soc.* 111:2339–2341 [1989]), the convergent growth strategy of Fréchet and co-workers (Hawker et al., *J. Chem. Soc. Perkins Trans.* 12:1287–1297 [1993]; Fréchet, *Science* 263:1710–1715 [1994]; and Fréchet, *Science* 269:1080–1083 [1995]), and the self-assembly strategy of Zimmerman and co-workers (Zimmerman et al., *Science* 271:1095–1098 [1996]). These methods have made possible the generation of synthetic macromolecules with unique combinations of properties (Bell, *Science* 271:1077–1078; van Hest et al., *Science* 268:1592–1595 [1995]; Jansen et al., *J. Am. Chem. Soc.* 117:4417–4418 [1995]; and Jansen et al., *Science* 266:1226–1229 [1995]).

SUMMARY OF THE INVENTION

The present invention relates to compositions and methods involving biocompatible dendrimers. In particular, the present invention provides dendrimeric copolymers with poly(propyleneimine) (POPAM) interiors and poly (amidoamine) (PAMAM) exteriors for use in transfection and imaging applications.

For example, the present invention provides a composition comprising a hybrid dendrimer having a poly (propyleneimine) interior and a poly(amidoamine) exterior. In some embodiments, the poly(propyleneimine) interior is a dendrimer selected from the group consisting of a generation 2 dendrimer with sixteen amine surface groups, a generation 3 dendrimer with 32 amine surface groups, and a generation 4 dendrimer with 64 amine surface groups, although other dendrimers may be used. In some embodiments, the poly(amidoamine) exterior comprises one or more shells (e.g., 1, 2, 3, 4, 5, etc.). In some preferred embodiments, the hybrid dendrimer has a 1,4-diaminobutane core.

In some embodiments, the hybrid dendrimer further comprising a guest molecule. The present invention is not limited by the nature of the guest molecule. A number of exemplary guest molecules are disclosed herein. In some preferred embodiments, the guest molecule comprises a nucleic acid molecule, a metal, and/or a drug.

The present invention also provides methods for preparing a hybrid dendrimer comprising: providing an amine-terminated poly(propyleneimine) dendrimer, methyl acrylate, and ethylenediamine; reacting said amine-terminated poly(propyleneimine) dendrimer with said methyl acrylate to produce an ester-terminated compound; and reacting said ester-terminated compound with ethylenediamine to produce said hybrid dendrimer. In some embodiments, the method further comprises the step of d) attaching a guest molecule to said hybrid dendrimer. In some embodiments, the amine-terminated poly(propyleneimine) dendrimer comprises a guest molecule (e.g., which gets incorporated into the hybrid dendrimer when the out layers are added). In some preferred embodiments, the reacting steps are conducted in a methanol solvent under an intert nitrogen atmosphere. The present invention provides compositions comprising the hybrid dendrimer prepared according to such methods. In some embodiments, the hybrid dendrimer has a hydrodynamic diameter of from 10 to 100 angstroms.

The present invention also provides methods for transfecting cells comprising: providing dendrimer/nucleic acid complexes and target cells; and ballistically accelerating the dendrimer/nucleic acid complexes at the target cells under conditions such that nucleic acid enters the target cells. In some embodiments, the dendrimer/nucleic acid complexes comprise PAMAM dendrimers. In some embodiments, the dendrimer/nucleic acid complexes comprise hybrid dendrimers having a poly(propyleneimine) interior and a poly (amidoamine) exterior. In some preferred embodiments, the dendrimer/nucleic acid complexes comprise metal particles (e.g., gold and/or silver particles). In some preferred embodiments, the dendrimer/nucleic acid complexes have a charge ratio of 1 or less (e.g., 0.1 or less). In some preferred embodiments, the dendrimer/nucleic acid complexes comprise 99% or greater monodispersed particles. In some embodiments, the ballistically accelerating step is carried out by a ballistic device. In some preferred embodiments, the ballistic device is held less than one centimeter from said target cells during said ballistically accelerating step.

DESCRIPTION OF THE FIGURES

The following figures form part of the specification and are included to further demonstrate certain aspects and embodiments of the present invention. The invention may be better understood by reference to one or more of these figures in combination with the detailed description of specific embodiments presented herein.

DEFINITIONS

Figure 1:
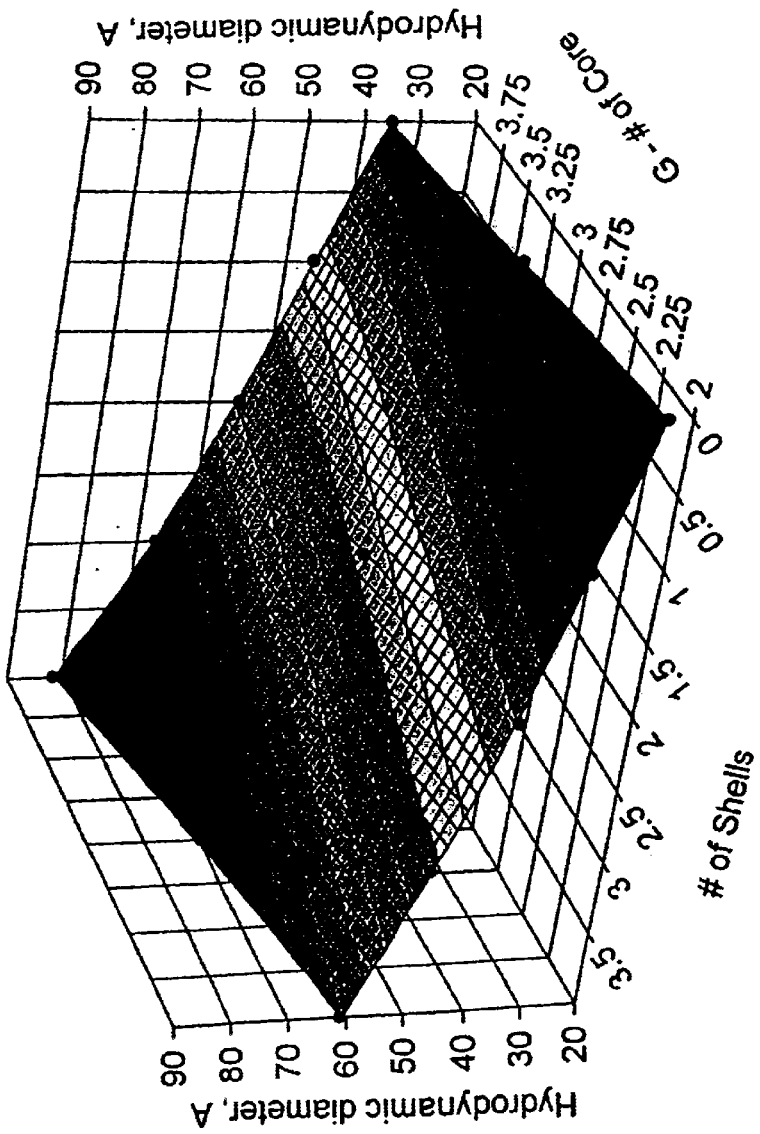
FIG. 1 shows that the hydrodynamic diameter of the POMAM hybrid dendrimers is a function of the generation number and the number of shells.

To facilitate an understanding of the present invention, a number of terms and phrases are defined below:

As used herein, the terms "biocompatible" and "biofriendly" refer to compositions comprised of natural or synthetic materials, in any suitable combination, that remain substantially biologically unreactive in a host. The term "substantially unreactive" means that any response observed in a host is a subclinical response (e.g., a response that does not necessitate therapy). The term "gene" refers to a nucleic acid (e.g., DNA) sequence that comprises coding sequences necessary for the production of a polypeptide or precursor. The polypeptide can be encoded by a full length coding sequence or by any portion of the coding sequence so long as the desired activity or functional properties (e.g., enzymatic activity, ligand binding, signal transduction, etc.) of the full-length or fragment are retained. The term also encompasses the coding region of a structural gene and the including sequences located adjacent to the coding region on both the 5' and 3' ends for a distance of about 1 kb or more on either end such that the gene corresponds to the length of the full-length mRNA. The sequences that are located 5' of the coding region and which are present on the mRNA are referred to as 5' non-translated sequences. The sequences that are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the term "antisense" is used in reference to DNA or RNA sequences that are complementary to a specific DNA or RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter which permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

Where amino acid sequence is recited herein to refer to an amino acid sequence of a naturally occurring protein molecule, amino acid sequence and like terms, such as polypeptide or protein are not meant to limit the amino acid sequence to the complete, native amino acid sequence associated with the recited protein molecule.

The term "transgene" as used herein refers to a foreign gene that is placed into an organism. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, are used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

As used herein, the term "gene transfer system" refers to any means of delivering a composition comprising a nucleic acid sequence to a cell or tissue. For example, gene transfer systems include, but are not limited to vectors (e.g., retroviral, adenoviral, adeno-associated viral, and other nucleic acid-based delivery systems), microinjection of naked nucleic acid, dendrimers, and polymer-based delivery systems (e.g., liposome-based and metallic particle-based systems). As used herein, the term "viral gene transfer system" refers to gene transfer systems comprising viral elements (e.g., intact viruses and modified viruses) to facilitate delivery of the sample to a desired cell or tissue.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, biolistics, and dendrimers.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

As used herein, the term "recombinant DNA molecule" as used herein refers to a DNA molecule that is comprised of segments of DNA joined together by means of molecular biological techniques.

The term "test compound" refers to any chemical entity, pharmaceutical, drug, and the like that can be used to treat or prevent a disease, illness, sickness, or disorder of bodily function. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense and includes environmental and biological samples. Environmental samples include material from the environment such as soil and water. Biological samples may be animal, including, human, fluid (e.g., blood, plasma and serum), solid (e.g., stool), tissue, liquid foods (e.g., milk), and solid foods (e.g., vegetables).

DESCRIPTION OF THE INVENTION

Two major dendrimer compositions that are produced commercially using a divergent synthetic strategy include: poly(amidoamine) or PAMAM dendrimers and poly(propyleneimine) or POPAM dendrimers. PAMAM dendrimers with ethylene diamine cores are produced by Dendritech Incorporated of Midland, Mich. (Tomalia et al., Angew. Chem. Intl. Edit. 29:138–175 [1990]; and Naylor et al., J. Am. Chem. Soc. 111:2339–2341 [1989]), while POPAM dendrimers with diaminobutane cores are produced by DSM of Herleen, The Netherlands (De Brabander et al., Angew. Chem. Int. Ed. 32:1308 [1993]; and De Brabander et al., Macromol. Symp. 102:9 [1996]). PAMAM dendrimers are remarkably biofriendly synthetic substances that have been incorporated into a considerable number of experimental diagnostic and therapeutic compositions. Unfortunately, the production of high generation PAMAM dendrimers, capable of encapsulating guest molecules requires numerous synthetic rounds making these compounds costly and potentially less than monodisperse. POPAM dendrimers, in contrast, can be produced to higher dimensions with fewer synthetic rounds thus yielding a potentially more homogenous product at a reduced cost. The use of POPAM dendrimers, however, is typically limited to plastics, inks, adhesives, and catalysts, as POPAM dendrimers are fairly toxic to biological systems. Thus, new types of dendrimers are needed for various applications in the life sciences. In particular, new dendrimer compositions are desirable for drug delivery, medical imaging, and gene transfection purposes.

To meet this need, the present invention provides novel dendrimeric copolymers composed of biocompatible PAMAM exteriors and low cost POPAM interiors. These hybrid dendrimers (POPAM+PAMAM=POMAM) can be synthesized from a low generation POPAM dendrimer core according to a reiterative process involving sequential Michael addition and amidation. Thus, the POMAM dendrimers of the present invention, which are synthesized at a reduced cost as compared to similar sized PAMAM dendrimers, are expected to be biocompatible vehicles for drugs, contrast agents or nucleic acids.

1. POMAM Dendrimers

Briefly, the preparation of POMAM hybrid dendrimers involves a divergent synthesis consisting of two reiterating reactions. The first reaction is a step growth process that involves Michael addition of amino groups to the double bond of methyl acrylate (MA). The second reaction is a chain growth process that involves amidation of the resulting terminal methyl ester with ethylenediamine (EDA).

In the first step of this process, POPAM dendrimers of generation 2, 3, or 4, with 16, 32, or 64 primary amine groups on their surfaces, were allowed to react under an inert nitrogen atmosphere with excess MA at room temperature for 24–48 hours, with the amount of time varying proportionally with the number of primary amine groups on the starting material. The resulting compounds are referred to as half generation POMAM hybrid dendrimers. The second step of the process involves reacting the newly-formed terminal esters with excess EDA to produce a PAMAM shell around the POPAM dendrimer. The amidation reactions were performed under inert nitrogen atmosphere in methanol at 2° C. and also require 24–48 hours for completion. Thus, POMAM hybrid dendrimers of the invention have twice as many primary amine groups on their surface as did the starting material.

$^{13}$C NMR spectroscopy is a sensitive measurement of the magnetic environment of every carbon atom in a compound. The highly symmetrical POPAM, PAMAM, and POMAM dendrimer structures places all of the terminal groups in an almost equivalent magnetic environment, yielding very simple spectra for molecules of such high molecular weights. Any deviations from this symmetry, perhaps caused by errors in synthesis or degradation of the material, are indicated by additional signals in the $^{13}C$ NMR spectrum (e.g., corresponding to the carbon atom in the vicinity of the structural defect). A representative example of a $^{13}C$ NMR spectrum of a generation 2:1 POMAM dendrimer was essentially the superposition of the spectra of POPAM and PAMAM dendrimers. A peak at approximately 175 ppm was observed that clearly indicated the PAMAM shell incorporation with the POPAM dendritic core.

The theoretical and experimental molecular weights of the dendrimers are dependent upon the generation number of the POPAM core and the number of PAMAM shells added to the core. Experimental molecular weights were determined by GPC. Lower generation POMAM hybrid dendrimers (2:1, 2:2, 3:1, 3:2, 4:1, and 4:2) exhibited a very narrow distribution in molecular weight indicating that these dendrimers were relatively monodisperse. Higher generation POMAM hybrid dendrimers (e.g., 2:3, 2:4, 3;3, 3;4, 4:3, and 4:4), in contrast, exhibited a narrow, bimodaldistribution in molecular weight. The second, higher molecular weight peak, accounted for less than 10% of the area of the first, lower molecular weight peak. The higher molecular weight peak may correspond to that of aggregated dendrimers as the conditions used for GPC would be expected to allow aggregation to take place. That said, the aggregation behavior of the higher molecular weight hybrid dendrimer was not observed on the HPLC eluogram. A HPLC eluogram comparing the generation2:2 POMAM dendrimer with the PAMAM dendrimers of generations 0 through 7. The comparison clearly indicates that the hydrodynamic volume of the generation2:2 POMAM dendrimer lies between the hydrodynamic values of the generation 3 and 4 PAMAM dendrimers.

FIG. 1 depicts the hydrodynamic diameter of the POMAM dendrimers as a function of the generation number of the core and the number of shells covering the core. The relation is almost linear and reaches a peak value of approximately 83 angstroms.

HPLC eluograms of POMAM hybrid dendrimers of generations 2:4, 3:4 and 4:4 indicate the dendrimer preparations are relatively pure as evidenced by the appearance of a single narrow major peak. Only a small amount of a higher molecular weight entity is present, which is in all likelihood due to aggregation of the lower molecular weight species. The inconsistent appearance of aggregates suggests that this behavior is highly influenced by the environment of the molecules. POMAM dendrimers asymptotically approach the liquid chromotographical properties of the PAMAM dendrimers.

The goal of obtaining high resolution AFM images of individual POMAM hybrid dendrimers was challenging as dendrimer molecules possess a high concentration of surface functional groups, which often causes them to aggregate. High resolution images of individual PAMAM, POPAM, or POMAM hybrid dendrimers of generation 5 or lower are difficult to obtain because of this problem (Jackson et al., *Macromolecules* 31:6259 [1998]). The larger dendrimers, however, and particularly the hybrid dendrimers, can be spread on a mica surface to show individual molecules in ultra-dilute solutions. Spin-coating techniques are also helpful in preparing uniform dendrimer films. In AFM images of a generation 4:3 hybrid dendrimer the globular particles which are randomly deposited on the mica surface are substantially uniform in size indicating that they are essentially monodisperse. Although a few aggregates are present, most of the clusters represent single molecules.

It is well known that ionic strength, surface charge density, and concentration or molecular environment are the important parameters controlling the degree of structural organization of the solution (Nisato et al., Macromolecules 32:5895–5900 [1999]). Addition of a monovalent salt such as potassium chloride or sodium chloride screens the long range electrostatic interactions and leads to a gas-like structure (e.g., disaggregated arrangement). Full generation dendrimers have a high density of primary amino groups on their surface. In that case, the surface charge densities of these molecules can be manipulated by varying the pH of the solution, permitting the dendrimers to be viewed as nanoscopic polyelectrolyte particles.

Importantly, the POMAM dendrimers involve two sorts of amine groups. The primary amine end groups ($-NH_2$) are on the dendrimer periphery, and their number is equal to $2^{(n+m+2)}$, with n representing the generation of the POPAM core, and m representing the number of PAMAM shells. The tertiary amine groups (>N—) are situated at the branching points in the molecule, and their number is equal to $2^{(n+m+2)}-2$. These two types of amine groups if isolated, are characterized by different pK values (Van Genderen et al., *Polym. Mater. Sci. Eng.* 73:336 [1995]), which are negative logarithms of the acidic dissociation constant for the protonated primary ($pK^{pr}$) and tertiary ($pK^t$) amine groups correspondingly. The basicity of the primary amine group is higher compared with that of the tertiary one (e.g., $pK^{pr}$ is greater than $pK^t$).

Figure 2:
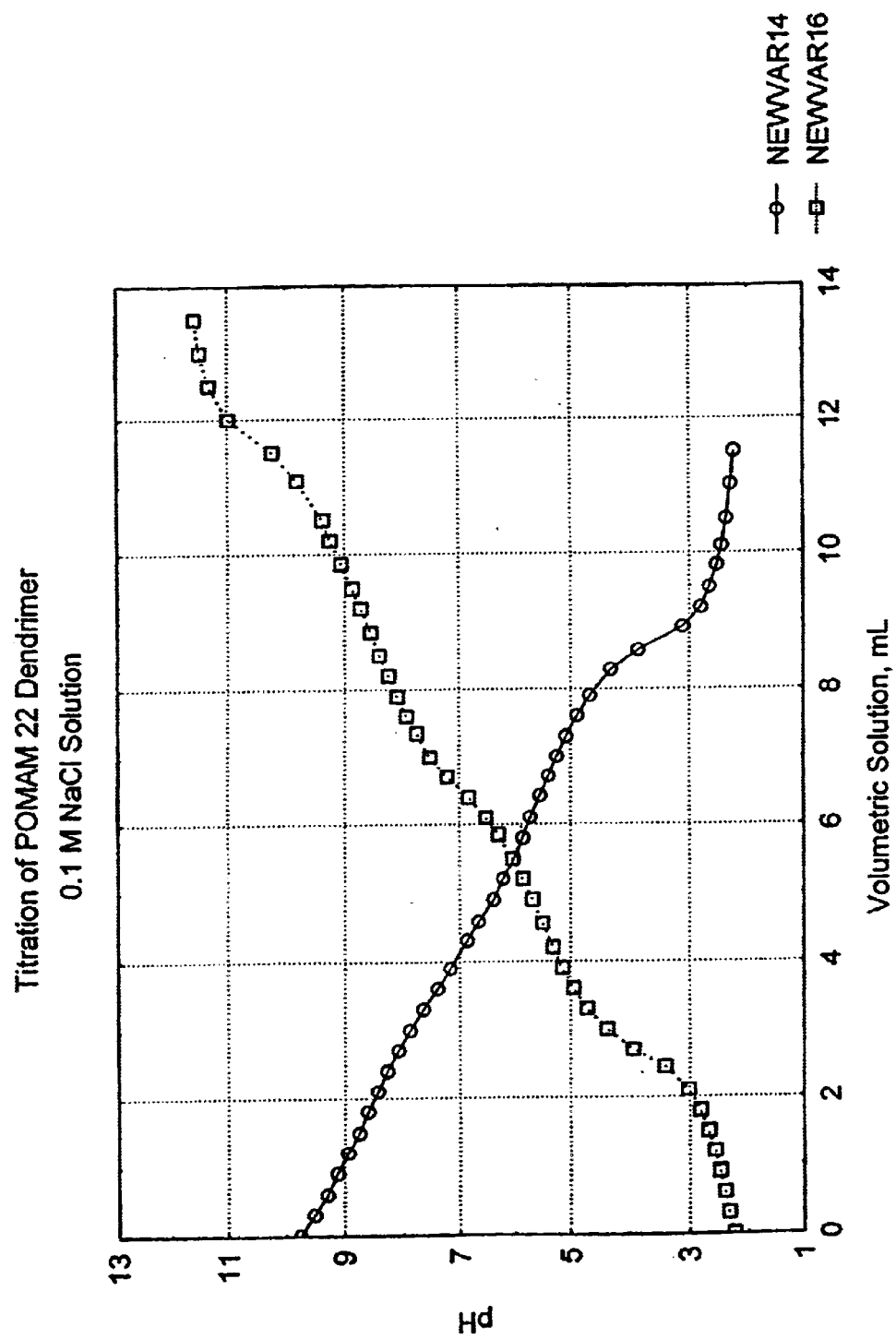
FIG. 2 shows the potentiometric tritration curve of the generation 2:2 POMAM hybrid dendrimer.

The protonation behavior of the dendrimers was studied by potentiometric titration. FIG. 2 shows a representative result obtained for a generation 2:2 POMAM dendrimer, titrated with 0.1 N HCl. Clearly, two sections can be distinguished, one for the primary amines at a high pH and one for the tertiary amines at a lower pH. The degree of protonation, which separates the regions was found to be equivalent to the ratio between the primary and secondary amines. The back titration, done with 0.1 N NaOH, shows three sections representing three acids present in the solution. The first section corresponds to excess HCl, the second to the tertiary amine, and the third to the protonated primary amine, respectively. The primary amine groups on the surface of the dendrimer are the most basic amino moieties of the dendrimer with a $pK_apr$ of ~8.9. In contrast, the tertiary amines have a $pK_at$ of ~5.6.

Thus, monodisperse POMAM hybrid dendrimers with POPAM cores and PAMAM shells were prepared using MA Michael addition and EDA amidation steps under controlled conditions. The POPAM cores used were generation 2, 3, and 4 dendrimers with 16, 32, and 63 primary amines, respectively. The observed 13C NMR, molecular weights, and hydrodynamic diameters were close to the theoretical values. Moreover, the AFM image indicates that the POMAM hybrid dendrimers were of a relatively uniform size.

II. Utilities

The following description provides exemplary utilities of the dendrimers of the present invention. These utilities find use with the POMAM dendrimers of the present invention as well as other dendrimers (e.g., PAMAM dendrimers). The following applications are not intended to be limited to the use of POMAM dendrimers.

A. Gene Transfection

Many previous studies have described methods to achieve transfection of cells in vitro and in vivo that employ the use of a device to accelerate expression plasmid DNA (Lin et al., *Int. J. Derm.* 39:161–170 [2000]; and Mahvi et al., *Immunol. Cell Bio.* 75:456–460 [1997]). The expression plasmid DNA can be administered either alone (e.g., "naked" DNA) or coated onto the surface of metal particles such as elemental gold or tungsten (Lai et al., DNA Cell Biol. 14:643–651 [1995]), through the use of polycations (e.g., spermidine or PLG; See Chen et al., J. Virol. 72:5757–5761 [1998]). There are inherent problems associated with both strategies.

"Naked" plasmid DNA is subject to structural damage by application of shear forces during acceleration and deceleration. In addition "naked" DNA is not a "solid" particle, it is a hydrodynamic circular double helix polymer that can be easily deformed during both acceleration and deceleration. As a result, "naked" DNA used as a ballistic particle does not penetrate tissue and cell membranes well.

There are also inherent problems with the use of DNA bound to metal particles. Elemental metal particles are large in size and when accelerated develop significant kinetic energy that causes significant nonspecific trauma to tissues and cells. Because the process of binding expression plasmid DNA to the metal particles is indirect (e.g., involves several steps of mixing small molecules with metal particles), there is no reliable method to adjust the stoichiometry of DNA molecules bound per metal particle. Moreover, the manufacture of DNA coated heavy metal particles is not readily scaleable.

The use of biocompatible dendrimers (i.e., PAMAM or POMAM hybrids) using the methods of the present invention as carriers for ballistic delivery of expression plasmid DNA obviates the problems associated with previously described systems. In fact PAMAM dendrimers have been successfully used as the DNA carriers for both in vitro and in vivo transfections (Bielinska et al., *Bioconjugate Chemistry* 10:843–850 [1999]; Bielinska et al., *Biomaterials* 21:877–887 [2000]; and Kukowska-Latallo et al., *Hum. Gene Ther.* 11:1385–1395 [2000]). The presence of negatively charged amino groups on the surface of dendrimers with PAMAM shells, allows for electrostatic interactions with various forms of nucleic acids. In addition, PAMAM dendrimers are non-immunogenic and biocompatible at the concentrations used in the formulations of dendrimer-DNA complexes described herein.

Experiments conducted during the development of the present invention demonstrate that utility of ballistic transfection using dendrimers. There are numerous advantages conferred by the use of PAMAM terminated dendrimer/DNA complexes for ballistic transfection of cells in vitro and in vivo. In the first place, PAMAM-terminated dendrimers protect expression plasmid DNA from shear-induced damage during acceleration and deceleration. Secondly, PAMAM-terminated dendrimers allow for manufacture of DNA complexes with specific and reproducible stoichiometric ratios and surface charges (e.g., zeta potential). These properties are important in determining the efficiency of ballistic mediated transfection, and the manufacture of the dendrimer/DNA particles is readily scaleable. Thirdly, PAMAM terminated dendrimer-DNA complexes are of consistent size and mass and can be formulated as a relatively monodisperse suspension. Fourthly, because the mass of the PAMAM terminated dendrimer-DNA complexes is substantially less than that of heavy metal particles, the kinetic energy of the complexes can be finely regulated in order to optimize cell membrane penetration and minimize nonspecific cell trauma. Lastly, because PAMAM-terminated dendrimers can be readily derivatized during manufacture, moieties designed to alter mass or provide targeting or biochemical function can be added to the polymers to optimize properties favorable for ballistic delivery. (Balogh et al., *J. Nanoparticle Research* 1:353–369 [1999]).

In summary, the results obtained from using in situ and in vivo model systems suggest that the use of dendrimer-DNA complexes for ballistic transfection of cells is significantly more efficient than the use of "naked" plasmid DNA. Specifically, greater transfection efficiency is defined as a higher level of transgenic protein expression for a given dose of administered DNA. Equally important, dendrimer/DNA complexes obviate many of the inherent technical and manufacturing problems associated with ballistic delivery of "naked" plasmid DNA or DNA indirectly bound to elemental heavy metal particles.

Examples 3–6 below provide a description of some preferred embodiments of the methods of the present invention.

B. Medical Imaging

In some embodiments of the present invention, dendrimers are used for medical imaging purposes by associating an imagable component with the dendrimer. The present invention is not limited by the nature of the imaging component used. In some embodiments of the present invention, imaging modules comprise surface modifications of quantum dots (See e.g., Chan and Nie, Science 281:2016 [1998]) such as zinc sulfide-capped cadmium selenide coupled to biomolecules (Sooklal, Adv. Mater., 10: 1083 [1998]).

However, in preferred embodiments, the imaging module comprises dendrimers produced according to the "nanocomposite" concept (Balogh et al., Proc. of ACS PMSE 77:118 [1997] and Balogh and Tomalia, J. Am. Che. Soc., 120:7355 [1998]). In these embodiments, dendrimers are produced by reactive encapsulation, where a reactant is preorganized by the dendrimer template and is then subsequently immobilized in/on the polymer molecule by a second reactant. Size, shape, size distribution and surface functionality of these nanoparticles are determined and controlled by the dendritic macromolecules. These materials have the solubility and compatibility of the host and have the optical or physiological properties of the guest molecule (i.e., the molecule that permits imaging). While the dendrimer host may vary according to the medium, it is possible to load the dendrimer hosts with different compounds and at various guest concentration levels. Complexes and composites may involve the use of a variety of metals or other inorganic materials. The high electron density of these materials considerably simplifies the imaging by electron microscopy and related scattering techniques. In addition, properties of inorganic atoms introduce new and measurable properties for imaging in either the presence or absence of interfering biological materials. In some embodiments of the present invention, encapsulation of gold, silver, cobalt, iron atoms/molecules and/or organic dye molecules such as fluorescein are encapsulated into dendrimers for use as nanoscopi composite labels/tracers, although any material that facilitates imaging or detection may be employed.

In some embodiments of the present invention, imaging is based on the passive or active observation of local differences in density of selected physical properties of the investigated complex matter. These differences may be due to a different shape (e.g., mass density detected by atomic force microscopy), altered composition (e.g., radiopaques detected by X-ray), distinct light emission (e.g., fluorochromes detected by spectrophotometry), different diffraction (e.g., electron-beam detected by TEM), contrasted absorption (e.g., light detected by optical methods), or special radiation emission (e.g., isotope methods), etc. Thus, quality and sensitivity of imaging depend on the property observed and on the technique used.

1. Magnetic Resonance Imaging

Dendrimers havebeen employed as biomedical imaging agents, perhaps most notably for magnetic resonance imaging (MRI) contrast enhancement agents (See e.g., Wiener et al., Mag. Reson. Med. 31:1 [1994]; an example using PAMAM dendrimers). These agents are typically constructed by conjugating chelated paramagnetic ions, such as Gd(III)-diethylenetriaminepentaacetic acid (Gd(III)-DTPA), to water-soluble dendrimers. Other paramagnetic ions that may be useful in this context of the include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

Dendrimeric MRI agents are particularly effective due to the polyvalency, size and architecture of dendrimers, which results in molecules with large proton relaxation enhancements, high molecular relaxivity, and a high effective concentration of paramagnetic ions at the target site. Dendrimeric gadolinium contrast agents have even been used to differentiate between benign and malignant breast tumors using dynamic MRI, based on how the vasculature for the latter type of tumor images more densely (Adam et al., Ivest. Rad. 31:26 [1996]). Thus, MRI provides a particularly useful imaging system of the present invention.

2. Microscopic Imaging

The dendrimers of the present invention allow functional microscopic imaging of tissues and provide improved methods for imaging. The methods find use in vivo, in vitro, and ex vivo. For example, in one embodiment of the present invention, dendrimers of the present invention are designed to emit light or other detectable signals upon exposure to light. Although the labeled dendrimers may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (Farkas et al., SPEI 2678:200 [1997]). In embodiments where the imaging agents are present in deeper tissue, longer wavelengths in the Near-infrared (NIR) are used (See e.g., Lester et al., Cell Mol. Biol. 44:29 [1998]). Dendrimeric biosensing in the Near-IR has been demonstrated with dendrimeric biosensing antenna-like architectures (Shortreed et al., J. Phys. Chem., 101:6318 [1997]). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue.

C. Therapeutic Agents

A wide range of therapeutic agents find use with the present invention. Any therapeutic agent that can be associated with a dendrimer may be delivered using the methods, systems, and compositions of the present invention.

Once inside the host cells or tissue, the biological agent has been either directly or indirectly delivered to the target. In some embodiments, without limitation, direct delivery of the agent means that the agent, with or without the associated dendrimer, is secreted from the cell into the extracellular space, where it acts upon the target tissue or is taken up by the target tissue.

In some embodiments, without limitation, indirect delivery means that the biological agent is modified in the cell prior to being secreted. Modification can take place either while the agent is still associated with the dendrimer or after disassociation of the components. For example, the biological agent may be in an inactive form and is rendered active following the introduction of the dendrimer complex to host cells or tissues. The biological agent, upon exposure to light or a change in pH (e.g., due to exposure to a particular intracellular environment), may be altered to assume its active form. Alternately, the agent may be attached to a protective linker (e.g., photo-cleavable, enzyme-cleavable, pH-cleavable) to make it inactive and become active upon exposure to the appropriate activating agent, e.g., UV light, a cleavage enzyme, or a change in pH. Indirect delivery may also comprise, in the case of transfection, the transcription of the nuclei acid to form a gene product, where the gene product is secreted to the extracellular space.

In other embodiments, the biological agent may not be secreted, but rather is retained within the cell where it may effect a change in the biological activities of host cell, either directly or through a series of signal transductions.

Degradation of the complex is useful because it eases the secretion of the biological agent, or transcription if the biological agent is a nucleic acid. The dendrimer complexes tend to degrade in a time-dependent manner under physiological conditions. Other dendrimer complexes resist degradation for a period of time under physiological conditions and then proceed to degrade. Degradation of the dendrimer complexes may be influenced by the surface chemistries of the dendrimers utilized. For example, particular dendrimer complexes may be selected or designed that degrade under particular physiological conditions or under an exogenous cue, e.g., heat, light, ultrasonic energy, and the like, provided either at administration, or at a selected biological event after administration.

In addition, dendrimer complexes may comprise one or more layers of dendrimer structure with one or more biological agents associated with each layer. This may allow for the release over time of biological agents as the layers of dendrimer degrade. If the same biological agent were used throughout the dendrimer, then a sustained release of biological agent would be obtained. Alternately, by using differing biological agents, a sequential release of agents may be accomplished. Indeed, multiple dissimilar agents may be associated with each layer of the dendrimer.

EXAMPLES

The following examples serve to illustrate certain preferred embodiments and aspects of the present invention and are not to be construed as limiting the scope thereof. In the experimental disclosure below, the following abbreviations apply: MA (methyl acrylate); EDA (ethylene diamine); MeOH (methanol); DAB (1,4-diaminobutane); NMR (nuclear magnetic resonance); SEC (size exclusion chromatography); HPLC (high performance liquid chromatography); AFM (atomic force microscopy); GPC (gas phase chromatography); luciferase (Luc); chloramphenicol acetyltransferase (CAT); eq (equivalents); μ (micron); M (Molar); μM (micromolar); mM (millimolar); N (Normal); mol (moles); mmol (millimoles); μmol (micromoles); nmol (nanomoles); g (grams); mg (milligrams); μg (micrograms); ng (nanograms); L (liters); ml (milliliters); μl (microliters); cm (centimeters); mm (millimeters); μm (micrometers); nM (nanomolar); ° C. (degrees Centigrade); PBS (phosphate buffered saline); hrs (hours); and RT (room temperature).

Example 1

POMAM Hybrid Dendrimer Syntheses

In this Example, the production of half and full generation POMAM hybrid dendrimers is described. Materials used for this purpose were purchased from Aldrich and include: methanol (MeOH) with 99.93% purity, ether, methyl acrylate (MA), and ethylenediamine (EDA). The purity of MeOH was 99.93%, while the purity of the remaining compounds was 99+%. EDA was distilled on a rotary evaporator at 2000 microns of mercury and a bath temperature of 36° C. The purified EDA was transferred to a vessel and stored at −4° C. under a $N_2$ blanket. The Astromol poly(propyleneimine) dendrimers of generations two through four (e.g., DAB-dendr-$(NH_2)_{16}$ to DAB-dendr-$(NH_2)_{64}$) were obtained from either DSM or Aldrich. Volumetric solutions of 0.1 M NaOH and 0.1 M HCl were also purchased from Aldrich, and used as received.

Generation 2:0.5, A: In a 50 ml three neck round bottom flask equipped with a magnetic stirrer, pressure equalized dropping funnel and condenser under a dry $N_2$ atmosphere, a solution of MA (6.41 ml, $7.114 \times 10^{-2}$ mol) in 7.7 ml MeOH was cooled to 0° C. Then a solution of 3 g ($1.7785 \times 10^{-3}$ mol) DAB-AM-16 polypropyleneimine hexadecaamine dendrimer (POPAM generation 2) in 10 ml MeOH (cooled to 0° C. under $N_2$) was added dropwise. This mixture was stirred under $N_2$ at 36° C. for 48 hrs, and the excess MA and MeOH was evaporated under a vacuum. To the residue, 3 ml water was added, mixed carefully, and after freezing was lyophilized to remove excess MeOH and MA, yielding a methyl-ester functionalized POPAM-core dendrimer, POMAM 2:0.5 (7.7 g, 97.5%).

Generation 2:0.5, B: To a mixture of MA (2.2495 g, $2.613 \times 10^{-2}$ mol) in 3 ml of MeOH cooled at 0° C. was added POPAM dendrimer (1,4-diaminobutane core, generation 2:0, with 16 $NH_2$ surface groups) (1.0203 g, $6.049 \times 10^{-4}$ mol) in 3.5 ml of MeOH cooled at 0° C. The resulting mixture was stirred at room temperature for 48 hrs. The MeOH and excess MA as volatiles were evaporated on a rotary evaporator at 34° C. and the resulting generation 2:0.5 dendrimer preparation was dried out at a vacuum of 500 microns of mercury to give 2.661 g (99.05%) of the title compound.

Generation 2:1: To a mixture of EDA (359.6 g, 5.9835 mol) in 100 ml of MeOH cooled at 0° C. was added POMAM hybrid dendrimer, generation 2:0.5 (1.0425 g, $2.347 \times 10^{-4}$ mol) in 3 ml of MeOH cooled at 0° C. This mixture was maintained at 0° C. for 48 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 1.246 g, 99.4% yield of the title compound.

Generation 2:1.5: To a mixture of MA (1.674 g, $194 \times 10^{-2}$ mol) in 2 ml of MeOH cooled at 0° C. was added POMAM hybrid dendrimer (generation 2:1, with 32 primary $NH_2$ surface groups; 1.2014 g, $2.25 \times 10^{-4}$ mol) in 5 ml of MeOH cooled to 0° C. The resulting mixture was stirred at room temperature for 48 hrs. The MeOH and excess MA as volatiles were evaporated on a rotary evaporator at 34° C. and the generation 2:1.5 dendrimer preparation was dried out under a vacuum of 500 microns of mercury to give 2.404 g (98.5%) of the title compound.

Generation 2:2: To a mixture of EDA (1438.4 g, 23.934 mol) in 400 ml of MeOH cooled to 0° C. was added POMAM hybrid dendrimer (generation 2:1.5; 2.186 g, $2.015 \times 10^{-4}$ mol) in 18 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 2.472 g, 97.02% yield of the title compound.

Generation 2:2.5: To a mixture of MA (1.31 g, $1.52 \times 10^{-2}$ mol) in 2 ml of MeOH cooled to 0° C. was added POMAM hybrid dendrimer (generation 2:2, with 64 $NH_2$ surface groups; 1.002 g, $7.92 \times 10^{-5}$ mol) in 5 ml of MeOH cooled to 0° C. The resulting mixture was stirred at room temperature for 72 hrs. The MeOH and excess of MA as volatiles were evaporated on a rotary evaporator at 34° C. and G-2:2.5 was dried out at a vacuum of 500 microns of mercury to give 1.804 g (96.2%) of the title compound.

Generation 2:3: To a mixture of EDA (2157.6 g, 35.901 mol) in 600 ml of MeOH cooled at 0° C. was added POMAM hybrid dendrimer (generation 2:2.5; 1.804 g, $7.62 \times 10^{-5}$ mol) in 16 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 1.6584 g, 79.8% yield of the title compound.

Generation 2:3.5: A mixture of MA (0.37 g, $4.3 \times 10^{-3}$ mol) in 1 ml MeOH cooled to 0° C. was added to a heterophase POMAM dendrimer (generation 2:3, with 128 $NH_2$ surface groups; 0.3052 g, $1.12 \times 10^{-5}$ mol) in 3 ml of MeOH cooled to 0° C. The resulting heterophase mixture was stirred at room temperature for 96 hrs. The MeOH and excess of MA as volatiles were evaporated on a rotary evaporator at 34° C. and the generation 2:3.5 dendrimer preparation was dried out under a vacuum of 500 microns of mercury to give 0.4387 g, 79.5% yield of the title compound.

Generation 2:4: To a mixture of EDA (1078.8 g, 17.95 mol) in 300 ml of MeOH cooled to 0° C. was added POMAM hybrid dendrimer (generation 2:3.5; 0.4387 g, $8.9 \times 10^{-6}$ mol) in 5 ml of MeOH cooled to 0° C. This mixture was maintained at 0° C. for 120 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 0.4963 g, 98.7% yield of the title compound.

Generation 3:0.5, A: In a 50 ml three neck round bottom flask equipped with magnetic stirrer, pressure equalized dropping funnel and condenser under dry $N_2$ atmosphere a solution of MA (5.41 ml, $6.008 \times 10^{-2}$ mol) in 6.5 ml MeOH was cooled to 0° C. Then a solution of 3 g ($7.511 \times 10^{-4}$ mol) DAB-Am-32 Polypropylenimine hexadecaamine dendrimer (generation 3:0) in 10 ml MeOH (also cooled to 0° C. under dry $N_2$) was added dropwise. This mixture was stirred under nitrogen at 34° C. for 48 hrs, and the excess MA and MeOH was evaporated in a vacuum. To the residue 3 ml of water was added, mixed carefully, and after freezing was lyophilized to remove excess MeOH and MA, yielding methyl-ester functionalized POPAM core dendrimer, POMAM 3:0.5, (7.02 g, 98.3%).

Generation 3:0.5, B: To a mixture of MA (2.2182 g, $2.577 \times 10^{-2}$ mol) in 3 ml of MeOH cooled at 0° C. was added POPAM dendrimer (1,4-diaminobutane core, generation 3:0, with 32 $NH_2$ surface groups; 1.1912 g, $3.39 \times 10^{-4}$ mol) in 3.5 ml of MeOH cooled to 0° C. The resulting mixture was stirred at room temperature for 48 hrs. The MeOH and excess MA as volatiles were evaporated on a rotary evaporator at 34° C. and generation 3:0.5 was dried out under a vacuum of 500 microns of mercury to give 3.0858 g, ~100% yield of the title compound.

Generation 3:1: To a mixture of EDA (719.2 g, 11.967 mol) in 200 ml of MeOH cooled to 0° C. was added POMAM hybrid dendrimer (generation 3:0.5; 1.0377 g, $1.15 \times 10^{-4}$ mol) in 13 ml of MeOH cooled to 0° C. This mixture was maintained at 0° C. for 48 hrs. After this reaction time the mixture was warmed to room temperature. The volatiles were removed from the mixture on a rotary evaporator at 34° C. with a vacuum at 2000–500 microns of mercury. The crude product was dissolved in MeOH and precipitated out by addition of ether. This purification process was repeated three times. The precipitate was dried very carefully to give 1.233 g, ~100% yield of the title compound.

Generation 3:1.5: To a mixture of MA (1.679 g, $1.95 \times 10^{-2}$ mol) in 2 ml of MeOH cooled to 0° C. was added POMAM hybrid dendrimer (generation 3:1, with 128 $NH_2$ surface groups; 1.2728 g, $1.176 \times 10^{-2}$ mol) in 5 ml of MeOH cooled to 0° C. The resulting mixture was stirred at room temperature for 48 hrs. The MeOH and excess of MA as volatiles were evaporated on a rotary evaporator at 34° C. and the generation 3:1.5 dendrimer preparation was dried out under a vacuum of 500 microns of mercury to give 2.451 g, 95.4% of the title compound.

Generation 3:2: To a mixture of EDA (2157.6 g, 35.901 mol) in 600 ml of MeOH cooled at 0° C. was added POMAM hybrid dendrimer (generation 3:1.5; 2.323 g, $1.064 \times 10^4$ mol) in 18 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 2.659 g, 98.3% yield of the title compound.

Generation 3:2.5: To a mixture of MA (1.615 g, $1.876 \times 10^{-2}$ mol) in 2 ml of MeOH cooled to 0° C. was added POMAM hybrid dendrimer (generation 3:2, with 128 $NH_2$ surface groups; 1.242 g, $4.88 \times 10^{-5}$ mol) in 5 ml of MeOH cooled to 0° C. The resulting mixture was stirred at room temperature for 72 hrs. The MeOH and excess MA as volatiles were evaporated on a rotary evaporator at 34° C. and generation 3:2.5 was dried out under a vacuum of 500 microns of mercury to give 2.185 g, 94.2% of the title compound.

Generation 3:3: To a mixture of EDA (5753.6 g, 95.736 mol) in 1600 ml of MeOH cooled to 0° C. was added POMAM hybrid dendrimer (generation 3:2.5; 2.185 g, $4.56 \times 10^{-5}$ mol) in 18 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 1.9742 g, 78.5% yield of the title compound.

Generation 3:3.5: A mixture of MA (0.37 g, $4.3 \times 10^{-3}$ mol) in 1 ml MeOH cooled to 0° C. was added to a heterophase POMAM dendrimer (generation 3:3, with 256 $NH_2$ surface groups; 0.3022 g, $5.5 \times 10^{-6}$ mol) in 3 ml of MeOH cooled to 0° C. The resulting heterophase mixture was stirred at room temperature for 96 hrs. The MeOH and excess MA as volatiles were evaporated on a rotary evaporator at 34° C. and the generation 3:3.5 dendrimer preparation was dried out under a vacuum of 500 microns of mercury to give 0.5088 g, 93.2% yield of the title compound.

Generation 3:4: To a mixture of EDA (2157.6 g, 35.9 mol) in 600 ml MeOH cooled to 0° C. was added POMAM hybrid dendrimer (generation 3:3.5; 0.5088 g, $5.2 \times 10^{-6}$ mol) in 15 ml of MeOH cooled to 0° C. This mixture was maintained at 0° C. for 120 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 0.5736 g, 98.4% yield of the title compound.

Generation 4:0.5, A: In a 50 ml three neck round bottom flask equipped with magnetic stirrer, pressure equalized dropping funnel and condenser under dry $N_2$ atmosphere a solution of MA (5.02 ml, $5.575 \times 10^{-2}$ mol) in 6.1 ml MeOH was cooled to 0° C. Then a solution of 3 g ($3.485 \times 10^{-4}$ mol) DAB-Am-64 Polypropylenimine hexadecaamine Dendrimer (generation 4:0) in 10 ml MeOH (also cooled to 0° C. under dry $N_2$) was added dropwise. This mixture was stirred under $N_2$ at 36° C. for 48 hrs, and the excess MA and MeOH was evaporated in a vacuum. To the residue 3 ml of water was added, mixed carefully, and after freezing was lyophilized to remove excess MeOH and MA, yielding methyl-ester functionalized POPAM-core dendrimer, POMAM 4:0.5, (6.83 g, 99.8%).

Generation 4:0.5, B: To a mixture of MA (1.7775 g, $2.065 \times 10^{-2}$ mol) in 2 ml of MeOH cooled to 0° C. was added POPAM dendrimer (1,4-diaminobutane core, generation 4:0, with 64 $NH_2$ surface groups; 1.0287 g, $1.435 \times 10^{-4}$ mol) in 3.5 ml of MeOH cooled to 0° C. The resulting mixture was stirred at room temperature for 48 hrs. The MeOH and excess MA as volatiles were evaporated on a rotary evaporator at 34° C. and the generation 4:0.5 dendrimer preparation was dried out under a vacuum of 500 microns of mercury to give 2.5112 g, 96.2% of the title compound.

Generation 4:1: To a mixture of EDA (1438.4 g, 23.934 mol) in 400 ml of MeOH cooled to 0° C. was added POMAM hybrid dendrimer, (generation 4:0.5; 1.0238 g, 5.63×10$^{-5}$ mol) in 13 ml of MeOH cooled to 0° C. This mixture was maintained at 0° C. for 48 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 1.21 g, ~100% yield of the title compound.

Generation 4:1.5: To a mixture of MA, (1.503 g, 1.75×10$^{-2}$ mol) in 2 ml of MeOH cooled to 0° C. was added POMAM hybrid dendrimer (generation 4:1, with 128 NH$_2$ surface groups; 1.1732 g, 5.39×10$^{-5}$ mol) in 5 ml of MeOH cooled to 0° C. The resulting mixture was maintained and stirred at room temperature for 48 hrs. The MeOH and excess of MA, as volatiles were evaporated on a rotary evaporator at 34° C. and the generation 4:1.5 dendrimer preparation was dried out under a vacuum of 500 microns of mercury to give 2.15 g, 91.4% yield of the title compound.

Generation 4:2: To a mixture of EDA (3596 g, 59.835 mol) in 1000 ml of MeOH cooled to 0° C. was added POMAM hybrid dendrimer (generation 4:1.5; 1.865 g, 4.26×10$^{-5}$ mol) in 18 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and was precipitated out by addition of ether. This purification process was repeated three times. The precipitate was dried very carefully to give 2.116 g, 97.4% yield of the title compound.

Generation 4:2.5: To a mixture of MA (1.32 g, 1.53×10$^{-2}$ mol) in 2 ml of MeOH cooled to 0° C. was added POMAM hybrid dendrimer (generation 4:2, with 256 NH$_2$ surface groups; 1.015 g, 1.99×10$^{-5}$ mol) in 5 ml of MeOH cooled to 0° C. The resulting mixture was stirred at room temperature for 72 hrs. The MeOH and excess MA as volatiles were evaporated on a rotary evaporator at 34° C. and the generation 4:2.5 dendrimer preparation was dried out under a vacuum of 500 microns of mercury to give 1.427 g, 75.4% yield of the title compound.

Generation 4:3: To a mixture of EDA (7192.0 g, 119.67 mol) in 2000 ml of MeOH cooled to 0° C. was added POMAM hybrid dendrimer (generation 4:2.5; 1.427 g, 1.48×10$^{-5}$ mol) in 15 ml of MeOH cooled to 0° C. This mixture was maintained at 0° C. for 72 hrs. After this reaction time the mixture was warmed to room temperature. The volatiles were removed from the mixture on a rotary evaporator at 34° C. with a vacuum at 2000–500 microns of mercury. The crude product was dissolved in MeOH and precipitated out by addition of ether. This purification process was repeated three times. The precipitate was dried very carefully to give 1.64 g, 99.8% yield of the title compound.

Generation 4:3.5: A mixture of MA (0.38 g, 4.4×10$^{-3}$ mol) in 1 ml of MeOH cooled to 0° C. was added to a heterophase POMAM dendrimer (generation 4:3, with 512 NH$_2$ surface groups; 0.3107 g, 2.8×10$^{-6}$ mol) in 3 ml of MeOH cooled to 0° C. The resulting heterophase mixture was stirred at room temperature for 96 hrs. The MeOH and excess MA as volatiles were evaporated on a rotary evaporator at 34° C. and the generation 4:3.5 dendrimer preparation was dried out under a vacuum of 500 microns of mercury to give 0.3922 g, 69.9% yield of the title compound.

Generation 4:4: To a mixture of EDA (2876.8 g, 47.9 mol) in 800 ml of MeOH cooled to 0° C. was added POMAM hybrid dendrimer (generation 4:3.5; 0.3922 g, 2.0×10$^{-6}$ mol) in 3 ml of MeOH cooled to 0° C. This mixture was maintained at 0° C. for 120 hrs. After this reaction time the mixture was warmed to room temperature. The volatiles were removed from the mixture on a rotary evaporator at 34° C. with a vacuum at 2000–500 microns of mercury. The crude product was dissolved in MeOH and precipitated out by addition of ether. This purification process was repeated three times. The precipitate was dried very carefully to give 0.4411 g, 98.2% yield of the title compound.

Example 2

POMAM Hybrid Dendrimer Characterization

In this Example, the techniques used to characterize the POMAM hybrid dendrimers of the present invention are described. The techniques utilized for characterization include: NMR, SEC, HPLC, potentiometric titration, and AFM.

For $^1$H and $^{13}$C NMR measurements, a Bruker AVANCE DRX 500 instrument was used. Approximately 30–40 mg/ml D$_2$O solutions was used for these investigations.

The SEC eluograms were obtained using an Alliance Waters 2690 Separation Module combined with triple detectors: Waters 2487 Dual Absorbance Detector, Wyatt DAWN DSP Laster Photometer, and Optilab DSP Interferometric Refractometer at 30° C. The module was equipped with a TosoHaas TSK-GEL Guard PWH (06762), 7.5×7.5 cm, 12 μm (DS 1140), G 2000 PW (05761), 10 μM (DS 1014), G 3000 PW (05762), 10 μM (DS 1016), and G 4000 PW (05763), 17 μm (DS 1017) columns. A 0.1 N citric acid solution (pH 2.72 adjusted with sodium hydroxide, and containing 0.025% sodium azide) was used as the mobile phase and for making sample solutions for SEC analysis. A nominal flow rate setting of 1.0 ml/min and an injection volume of 50 μl was used.

For HPLC measurements, a Beckman System Gold instrument was used which was equipped with a solvent module (126) and a UV detector (166). A 0.1 M trifluoroacetic acid eluent was used with a flow rate of 1 ml/min, in a C-18 reverse column at room temperature.

The potentiometric titration of dendrimers in aqueous solution was done using an ORION pH meter (model 230A) with and Oric glass combined electrode (5107 BN) at room temperature. For sample preparation, a 0.1 M NaCl solution was used, prepared from high purity NaCl (99.999%) and Milli-Q water (18 Mohm/cm).

For AFM measurements, samples on mica were examined using a TopoMetrix 2000 Discoverer instrument under ambient conditions. Ultrathin films of the POMAM hybrid dendrimers were prepared by spin-coating the dilute solutions on to freshly cleaved mica, which was air-dried at room temperature. It was not possible to obtain stable images using the contact mode, because the scanning tip appeared to move the molecules. This problem was circumvented by using the tapping mode for imaging. Si probes having a spring constant of ca. 30 N/m were used at a resonance frequency of ca. 200 to 300 kHz. A 7 μm scanner (x, y, and z directions) calibrated by TopoMetrix was used to collect the data.

Example 3

Preparation of Dendrimer-DNA Complexes and Particle Acceleration

In this Example, the preparation of PAMAM-terminated dendrimer/DNA complexes and the ballistic transfer of the dendrimer/DNA complexes is described. It is important to note that the invention is not necessarily specific to the method employed to achieve acceleration of the dendrimer/DNA complexes. An important component of the invention is the use of dendrimer/DNA complexes of a specific kinetic energy at the surface of the cells or tissues that are to be transfected.

Formulations of Dendrimer-DNA Complexes Used for Ballistic Transfection

Generation 5 EDA core PAMAM dendrimers were tested as a prototypic polymer, although the present invention is not limited to the use of PAMAM dendrimers. In some experiments, generation 5 EDA core PAMAM dendrimers were modified during manufacture to contain small amounts of silver (Ag) or gold (Au). Various formulations of dendrimer/DNA complexes were prepared in water, 0.09% NaCl or in the presence of modified -cyclodextrins. Size and population distribution of the dendrimer/DNA complexes was analyzed using a NICOMP Model 370 particle sizer. The complexes were formed in water with plasmid DNA at a concentration ranging from 0.05 mg/ml to 1 mg/ml and at the theoretical dendrimer/DNA charge ratios of 0.0 1, 0.1 and 1. Dynamic Laser Light Scattering (DLLS) analysis indicated that at the low charge ratios (e.g., 0.01 and 0.1) the mean dynamic diameter of the complex ranges from 5.3 to 59.7 nm depending upon the DNA concentration. However, complexes formed at the neutralizing charge ratio (e.g., 1.0) resulted in broadly polydispersed populations of particles containing the identifiable fractions with a mean dynamic diameter of 459 +/−29 nm (for a DNA concentration 0.05 mg/ml) and 909.4 +/−66.7 nm (for a DNA concentration of 0.1 mg/ml). The majority of particles existed in the form of large (>10 µm) aggregates and precipitates. The addition of the amphoteric-cyclodextrin at 0.05% or 0.1% (w/v) to dendrimer/DNA formulations resulted in the generation of almost monodispersed (>99%) particles with mean diameters of 5.3 +/−0.5 nm and 17 +/−11.4 nm respectively and complete disappearance of the aggregates. Formulations resulting in the most uniform distribution of dendrimer/DNA complexes of the 50 to 200 nm average particle size were used for the transfections.

During the development of the present invention, a commercially available hand held device was used to pneumatically accelerate the dendrimer/DNA complexes. The Biojector 2000 (Bioject) is a needle-free injection delivery system that utilizes compressed carbon dioxide as a power source for acceleration of materials in the form of aqueous solutions or suspensions.

Figure 3:
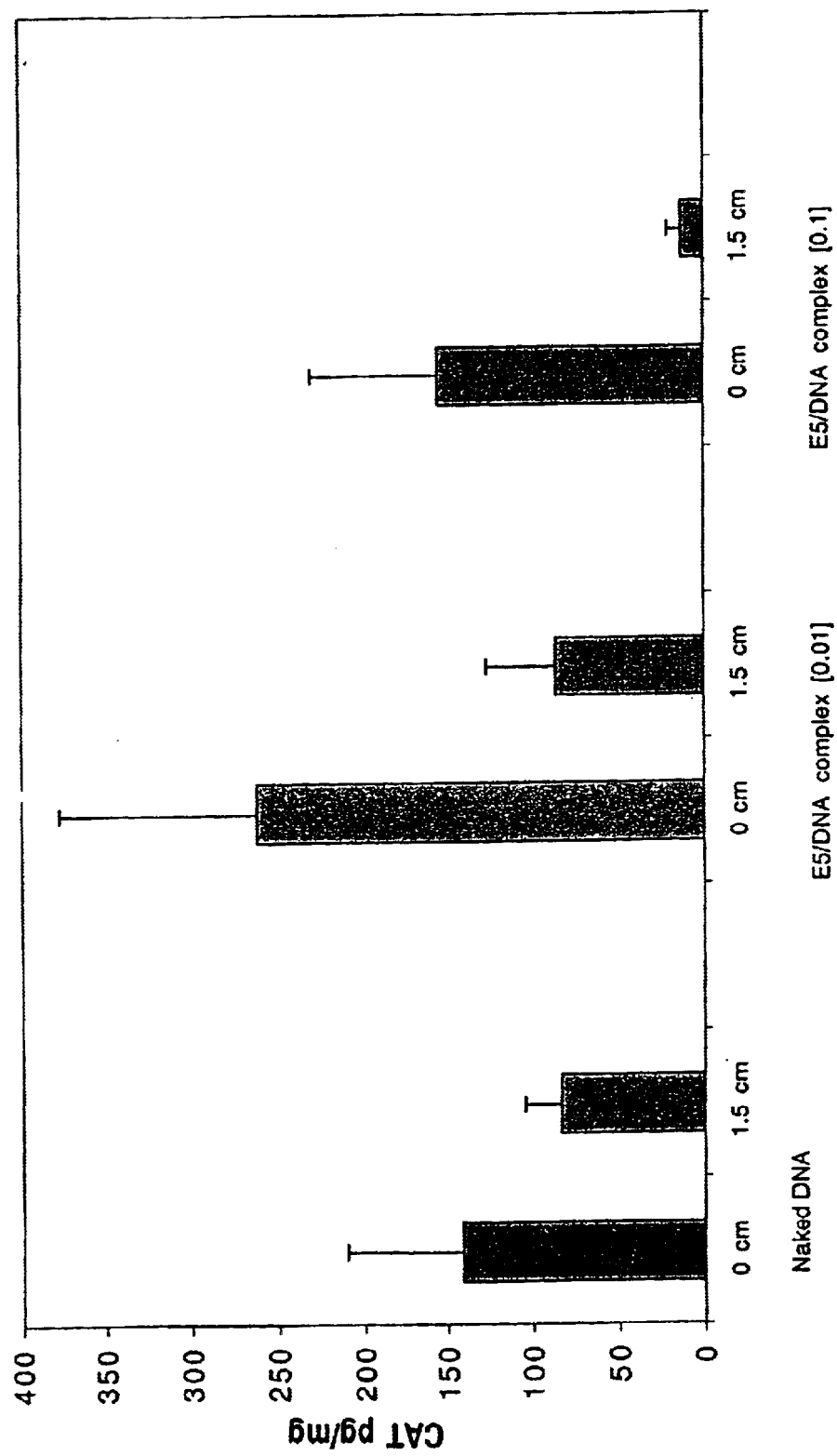
FIG. 3 shows the activity of the CAT transgene expressed by murine skin 48 hrs after in vivo ballistic delivery of generation 5 PAMAM dendrimer/DNA complexes. An orifice-to-target distance of 0 or 1.5 cm was used. The formulations of the samples are indicated along the x-axis, with the dendrimer/DNA charge ratio shown in parentheses.

The Biojector can deliver dendrimer/DNA complexes in volumetric unit doses of 50 to 200 µl. The distance from the Biojector pneumatic orifice to the surface of the target can be regulated using spacers of various lengths and diameters that can be attached to the Biojector. This orifice-target distance regulates the final kinetic energy of the particles at the time of contact with skin or tissue (FIG. 3). In the subsequent experiments, an orifice-target distance of 0 to 0.5 cm was found to be optimal for transfection of skin and mucosal cells.

All formulations tested contained a total of 100 µg plasmid DNA consisting of equal amounts of pCF1Luc, pCF1CAT and pCF1 gal suspended in a total volume of 100 µl water. Formulation I: DNA was complexed with 50 µg of Ag nanocomposite generation PAMAM dendrimers at an ~dendrimer/DNA charge ratio of 0.80. Formulation II: complexes were enriched with 6.5 µg of the unmodified dendrimer which increased the charge ratio to ~0.9. Formulation III: 0.05% amphoteric-cyclodextrin was added to Formulation II. Formulation IV: 0.05% sulphonated-cyclodextrin was added to formulation II.

Example 4

Ballistic Transfection of Human Skin with Dendrimer/DNA Complexes

Cadaveric split-thickness human skin was grafted onto the backs of SCID mice and used as a target for ballistic transfection. All ballistic transfections were done using a 1.5 cm adapter inserted into the micro-orifice of the Biojector device. The skin was harvested 24 hrs after ballistic transfection, as multiple 4 mm skin punch biopsies. Sonicated extracts of the punch biopsies were prepared and expression of both luciferase (Luc) and chloramphenicol acethyltransferase (CAT) was determined using established methods.

Figure 4:
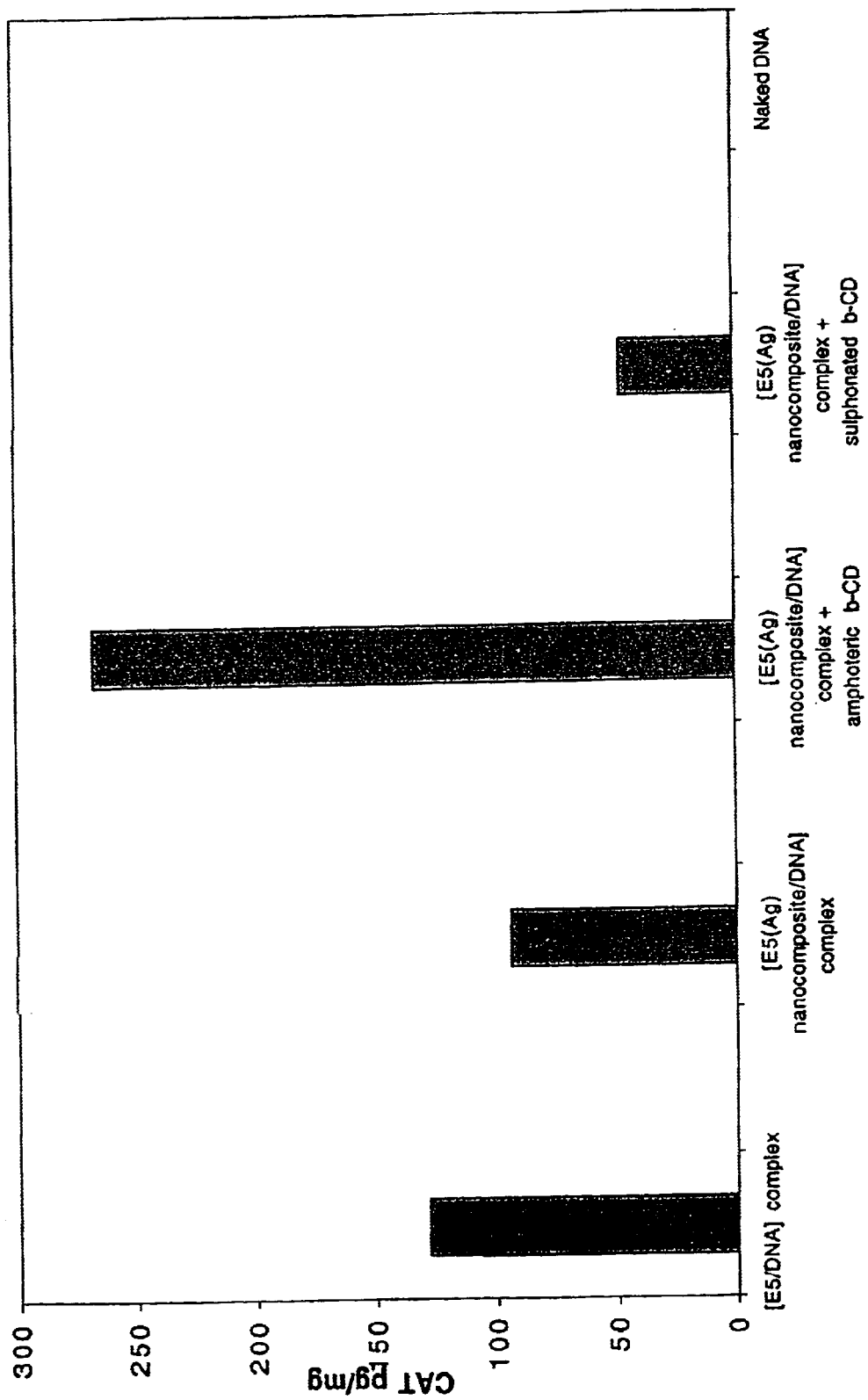
FIG. 4 shows the activity of the CAT transgene expressed by human skin grafts 24 hrs after ballistic delivery of dendrimer/DNA complexes. Human skin grafts established on the dorsal side of SCID mice were transfected with various dendrimer/DNA formulations as indicated along the x-axis.

Ballistic delivery of Formulations I and II resulted in similar levels of luciferase expression ($2.3 \times 10^5$ RLU/mg and $3.3 \times 10^5$ RLU/mg, respectively). CAT expression after transfection with Formulations I and II was found to be 84 and 47 pg/mg, respectively. Ballistic delivery of Formulation III, in contrast, resulted in a 5 to 7 fold increase in luciferase activity reaching ~$1.7 \times 10^6$ RLU/mg. Similarly, 120 pg/mg CAT protein was detected upon transfection with Formulation III. Formulation IV, containing sulphonated-cyclodextrin, was least effective and resulted in a 2 fold lower expression of both luciferase and CAT protein (FIG. 4).

The use of Ag or Au nanocomposite PAMAM dendrimers permitted the pharmacodistribution of the particles in skin following ballistic delivery to be determined by transmission electron microscopy (TEM). In particular, through TEM the histologic and ultrastructural localization of the particles was determined. In addition TEM was used to determine the location of dendrimer-DNA complexes as a function of the kinetic energy at the surface of the skin. In the preliminary TEM analysis of human skin grafts transfected with the nanocomposite PAMAM dendrimer/DNA complexes, irregular electron-dense deposits were detected in the experimental but not in the control sections. The localization of electron dense particles in intracellular and intranuclear locations, as well as, in the collagen-rich acellular matrix of the dermis was consistent with successful ballistic delivery of the dendrimer/DNA complexes.

Example 5

Ballistic Transfection of Murine Skin with Dendrimer/DNA Complexes

Figure 5:
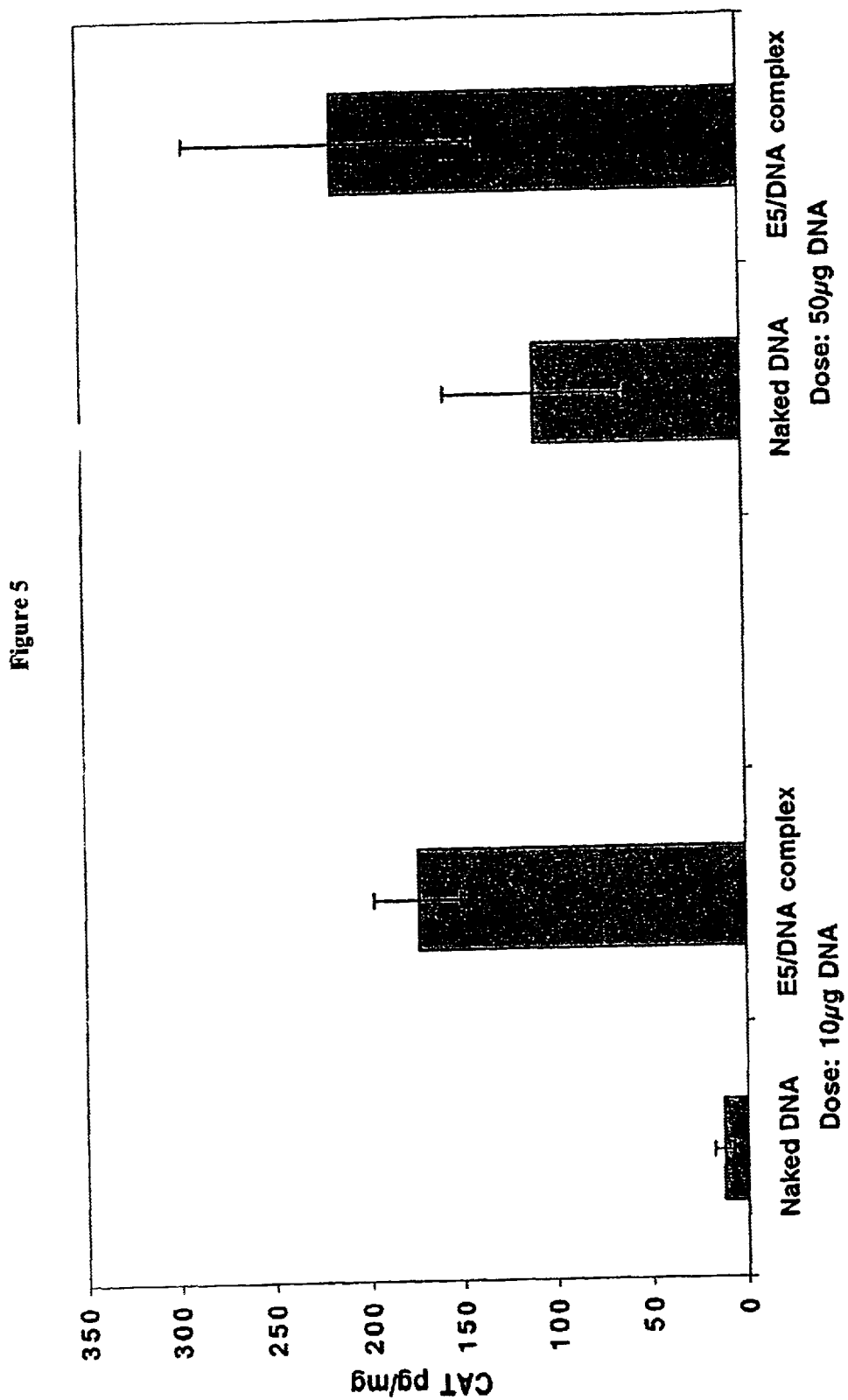
FIG. 5 shows the dose-dependent efficiency of dendrimer-mediated ballistic transfection of murine skin in vivo. Approximately 10 or 50 µg of reporter plasmid DNA was used alone or complexed with a generation 5 PAMAM dendrimer at 0.01 charge ratio. The CAT activity was measured 48 hr after transfection.

Dose dependence and efficacy of ballistic transfection using dendrimer/DNA complexes was tested in BALB/C mice. The shaved skin on the dorsal side of animals was transfected with 10 or 50 µg doses of pCF1CAT DNA alone or complexed with a PAMAM dendrimer. The dendrimer/DNA complexes at a charge ratio of 0.01 were prepared in 100 ml of water (e.g., DNA concentration of 0.5 and 0.1 mg/ml). All gene deliveries were performed without a spacer corresponding to an orifice-target distance equal to 0. Ballistic transfection using dendrimer/DNA complexes was found to be more efficient than "naked" DNA alone at DNA doses of 10 and 50 µg. The increase in transfection efficiency was most pronounced with decreasing doses of DNA, approximately 2 fold for 50 µg DNA and 13 fold for 10 µg DNA (FIG. 5). Additional ballistic transfections were done using a volumetric dose of 75 µl containing 10 or 50 µg "naked" DNA or DNA complexed to a generation 5 PAMAM dendrimer at a charge ratio of 0.05 and an orifice-target distance of 0.5 cm. Two days following ballistic transfection using 10 μg of DNA in the dendrimer/DNA complex, the level of transgene expression observed was similar to that obtained with 50 μg of "naked" DNA, and more than 80 fold higher than with 10 μg of "naked" DNA. Thus, ballistic transfection using dendrimer-DNA complexes minimizes the total dose of DNA required to achieve a given level of transgene expression in vivo.

Figure 6:
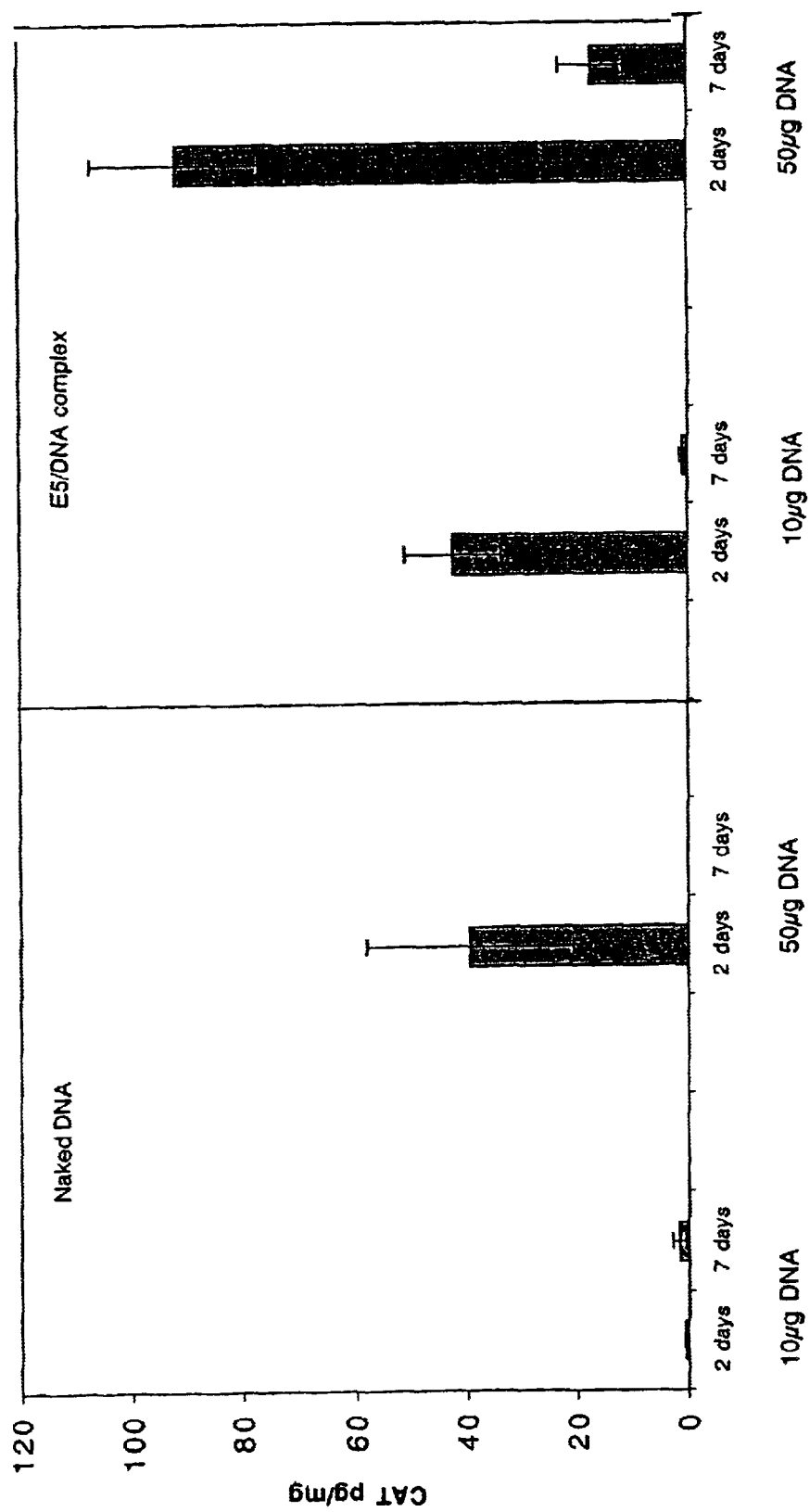
FIG. 6 shows the efficiency and duration of transgene expression following ballistic transfection of murine skin in vivo. BALB/c mice skin was transfected with the indicated amounts of either DNA alone or dendrimer/DNA complexes at 0.05 charge ratio. The CAT activity was measured 48 hr and 7 days after transfection.

In addition, the use of dendrimer/DNA complexes greatly prolonged the duration of the transgene expression in vivo. Murine skin was ballistically transfected using 10 or 50 μg of "naked" DNA or an equivalent dose of DNA complexed to a generation 5 PAMAM dendrimer. Seven days following transfection the levels of CAT protein detected in the samples treated with dendrimer/DNA complexes were 15–20% of the peak values, while samples treated with "naked" DNA were at the lower limits of assay detection (FIG. 6).

Example 6

Ballistic Transfection of Engineered Grafts with Dendrimer/DNA Complexes

The ballistic transfection of primary human oral mucosal keratinocytes, and primary dermal keratinocytes present within a tissue engineered material has also been accomplished during development of the present invention. The tissue engineered material (Alloderm) used for these experiments is suitable for intra-oral or dermal grafting (Izumi et al., *J. Dental Res.* 79:798–805 [2000]). Ballistic transfections of primary cell cultures of human fibroblasts and human oral keratinocytes grown on the surface of Alloderm were performed with generation 5 PAMAM dendrimers complexed to pCF1CAT, pCF1Luc, or pCMVhVEGF121. The pCMVhVEGF121 plasmid encodes a soluble form of vascular endothelial growth factor, an angiogenic protein that may have therapeutic value in the context of promoting wound repair and healing. Regardless of the cell type present within the tissue engineered Alloderm, efficient transfection was observed only in samples treated with PAMAM dendrimer-DNA complexes.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention, which are obvious to those skilled in relevant fields, are intended to be within the scope of the following claims.

We claim:

1. A composition comprising a hybrid dendrimer having a poly(propyleneimine) interior and a poly(amidoamine) exterior.

2. The composition of claim 1, wherein said poly(propyleneimine) interior is a dendrimer selected from the group consisting of a generation 2 dendrimer with sixteen amine surface groups, a generation 3 dendrimer with 32 amine surface groups, and a generation 4 dendrimer with 64 amine surface groups.

3. The composition of claim 1, wherein said poly(amidoamine) exterior comprises one or more shells.

4. The composition of claim 1, wherein said hybrid dendrimer has a 1,4-diaminobutane core.

5. The composition of claim 1, further comprising a guest molecule.

6. The composition of claim 5, wherein said guest molecule comprises a nucleic acid molecule.

7. The composition of claim 5, wherein said guest molecule comprises a metal.

8. The composition of claim 5, wherein said guest molecule comprises a drug.

9. The method for preparing a hybrid dendrimer comprising:

a) providing an amine-terminated poly(propyleneimine) dendrimer, methyl acrylate, and ethylenediamine;

b) reacting said amine-terminated poly(propyleneimine) dendrimer with said methyl acrylate to produce an ester-terminated compound; and c) reacting said ester-terminated compound with ethylenediamine to produce said hybrid dendrimer.

10. The method of claim 9, further comprising the step of d) attaching a guest molecule to said hybrid dendrimer.

11. The method of claim 9, wherein said amine-terminated poly(propyleneimine) dendrimer comprises a guest molecule.

12. The method of claim 9, wherein said reacting steps are conducted in a methanol solvent under an intert nitrogen atmosphere.

13. A composition comprising the hybrid dendrimer prepared according to the method of claim 9.

14. The composition of claim 13, wherein said hybrid dendrimer has a hydrodynamic diameter of from 10 to 100 angstroms.

* * * * *